United States Patent
Lin et al.

(10) Patent No.: US 9,494,574 B2
(45) Date of Patent: *Nov. 15, 2016

(54) T-CELL DEATH-INDUCING EPITOPES

(75) Inventors: Rong-Hwa Lin, Palo Alto, CA (US); Chung Nan Chang, Foster City, CA (US)

(73) Assignee: AbGenomics Cooperatief U.A., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/845,036

(22) Filed: Jul. 28, 2010

(65) Prior Publication Data

US 2011/0178270 A1    Jul. 21, 2011

Related U.S. Application Data

(63) Continuation of application No. 11/127,804, filed on May 11, 2005, now abandoned.

(60) Provisional application No. 60/570,161, filed on May 11, 2004.

(51) Int. Cl.
| | |
|---|---|
| C07K 7/08 | (2006.01) |
| G01N 33/50 | (2006.01) |
| C07K 5/107 | (2006.01) |
| C07K 5/113 | (2006.01) |
| C07K 5/117 | (2006.01) |
| C07K 7/06 | (2006.01) |
| C07K 14/47 | (2006.01) |
| A61K 38/00 | (2006.01) |

(52) U.S. Cl.
CPC ......... *G01N 33/5014* (2013.01); *C07K 5/1016* (2013.01); *C07K 5/1021* (2013.01); *C07K 5/1024* (2013.01); *C07K 7/06* (2013.01); *C07K 7/08* (2013.01); *C07K 14/4747* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,935,496 A | 6/1990 | Kudo et al. | |
| 5,378,464 A | 1/1995 | McEver | |
| 5,618,785 A | 4/1997 | Heavner et al. | |
| 5,709,859 A | 1/1998 | Aruffo et al. | |
| 5,710,123 A | 1/1998 | Heavner et al. | |
| 5,808,025 A | 9/1998 | Tedder et al. | |
| 5,827,817 A | 10/1998 | Larsen et al. | |
| 5,834,425 A | 11/1998 | Tedder et al. | |
| 5,840,679 A | 11/1998 | Larsen et al. | |
| 5,843,707 A | 12/1998 | Larsen et al. | |
| 5,852,175 A | 12/1998 | Cummings et al. | |
| 5,866,363 A | 2/1999 | Pieczenik | |
| 5,955,259 A * | 9/1999 | Holmes et al. | 435/4 |
| 5,972,625 A | 10/1999 | Rosen et al. | |
| 6,048,527 A | 4/2000 | Granoff et al. | |
| 6,056,956 A | 5/2000 | Cobbold et al. | |
| 6,124,267 A | 9/2000 | McEver et al. | |
| 6,309,639 B1 | 10/2001 | Cummings et al. | |
| 6,447,776 B1 | 9/2002 | Hofler et al. | |
| 6,534,277 B1 | 3/2003 | Hancock et al. | |
| 6,551,994 B1 | 4/2003 | Blaschuk et al. | |
| 6,559,294 B1 | 5/2003 | Griffais et al. | |
| 6,642,354 B2 | 11/2003 | Granoff et al. | |
| 7,063,949 B2 | 6/2006 | Granoff et al. | |
| 7,604,800 B2 | 10/2009 | Lin et al. | |
| 7,744,888 B2 | 6/2010 | Lin et al. | |
| 8,287,871 B2 | 10/2012 | Lin et al. | |
| 8,298,540 B2 | 10/2012 | Lin et al. | |
| 8,357,363 B2 * | 1/2013 | Weber et al. | 424/93.3 |
| 8,361,472 B2 | 1/2013 | Lin et al. | |
| 8,557,579 B2 | 10/2013 | Lin et al. | |
| 8,628,775 B2 | 1/2014 | Lin et al. | |
| 8,663,641 B2 | 3/2014 | Lin et al. | |
| 8,828,397 B2 | 9/2014 | Lin et al. | |
| 2002/0164336 A1 | 11/2002 | Harrison et al. | |
| 2003/0049252 A1 | 3/2003 | Lin et al. | |
| 2004/0001839 A1 | 1/2004 | Levanon et al. | |
| 2004/0002450 A1 | 1/2004 | Lazarovits et al. | |
| 2004/0116333 A1 | 6/2004 | Lin et al. | |
| 2004/0202650 A1 | 10/2004 | Gribben et al. | |
| 2004/0213766 A1 | 10/2004 | Francois | |
| 2004/0258708 A1 | 12/2004 | Jochmus et al. | |
| 2005/0152906 A1 | 7/2005 | Levanon et al. | |
| 2005/0266003 A1 | 12/2005 | Lin et al. | |
| 2006/0003940 A1 | 1/2006 | Lin et al. | |

(Continued)

FOREIGN PATENT DOCUMENTS

| | | | |
|---|---|---|---|
| WO | WO 97/06176 A2 | | 2/1997 |
| WO | WO 98/08874 | * | 3/1998 |

(Continued)

OTHER PUBLICATIONS

Kataoka et al ('Complete structure of eclosion hormone of Manduca sexta' Int J Peptide Protein Res v39 1992 pp. 29-35).*
BLAST search of PMEI (retrieved from http://blast.ncbi.nlm.nih.gov/Blast.cgi on Nov. 3, 2014, 28 pages).*
International Search Report and Written Opinion for PCT/US2005/016441 mailed Nov. 2, 2005.
Genbank Accession No. NP_623418. Bao et al. May 16, 2002. 2 pages.
Abbas et al., eds., Cellular and Molecular Biology, 4th Edition, 2000, W.B. Saunders, Philadelphia, p. 57.
Alderson et al., Fas ligand mediates activation-induced cell death in human T lymphocytes. J Exp Med. Jan. 1, 1995;181(1):71-7.

(Continued)

Primary Examiner — Christina Bradley
Assistant Examiner — Ronald Niebauer
(74) Attorney, Agent, or Firm — Wolf, Greenfield & Sacks, P.C.

(57) ABSTRACT

Cell death-inducing epitopes and polypeptides containing same. Also disclosed are compounds for inducing death of activated T-cells, a method of producing antibodies to the epitopes, a method of identifying compounds that bind to the epitopes, a method of inducing death of activated T-cells, and pharmaceutical compositions containing the compounds.

8 Claims, No Drawings

(56) References Cited

U.S. PATENT DOCUMENTS

| | | | |
|---|---|---|---|
| 2009/0191204 | A1 | 7/2009 | Lin et al. |
| 2009/0198044 | A1 | 8/2009 | Lin et al. |
| 2009/0304709 | A1 | 12/2009 | Lin et al. |
| 2010/0080819 | A1 | 4/2010 | Lin et al. |
| 2011/0172397 | A1 | 7/2011 | Lin et al. |
| 2013/0011391 | A1 | 1/2013 | Bassarab et al. |
| 2013/0011861 | A1 | 1/2013 | Lin et al. |
| 2013/0101587 | A1 | 4/2013 | Lin et al. |
| 2013/0102762 | A1 | 4/2013 | Lin et al. |
| 2013/0209449 | A9 | 8/2013 | Bassarab et al. |
| 2013/0251708 | A1 | 9/2013 | Bassarab et al. |
| 2014/0065176 | A1 | 3/2014 | Lin et al. |
| 2015/0183870 | A1 | 7/2015 | Lin et al. |

FOREIGN PATENT DOCUMENTS

| | | | |
|---|---|---|---|
| WO | WO 98/35985 | * | 8/1998 |
| WO | WO 00/25808 | A1 | 5/2000 |
| WO | WO 01/79555 | A2 | 10/2001 |
| WO | WO 02/22820 | A1 | 3/2002 |
| WO | WO 02/053700 | A2 | 7/2002 |
| WO | WO 03/006654 | * | 1/2003 |
| WO | WO 03/013603 | A1 | 2/2003 |
| WO | WO 2004/003166 | A2 | 1/2004 |
| WO | WO 2004/049907 | A2 | 6/2004 |
| WO | WO 2005/027831 | A2 | 3/2005 |
| WO | WO 2005/110456 | A2 | 11/2005 |
| WO | WO 2005/110475 | A1 | 11/2005 |
| WO | WO 2012/174001 | A1 | 12/2012 |

OTHER PUBLICATIONS

Battistini et al., CD8+ T cells from patients with acute multiple sclerosis display selective increase of adhesiveness in brain venules: a critical role for P-selectin glycoprotein ligand-1. Blood. Jun. 15, 2003;101(12):4775-82. Epub Feb. 20, 2003.

Beckwith et al., The protein product of the proto-oncogene c-cbl forms a complex with phosphatidylinositol 3-kinase p85 and CD19 in anti-IgM-stimulated human B-lymphoma cells. Blood. Nov. 1, 1996;88(9):3502-7.

Besnault et al., B cell receptor cross-linking triggers a caspase-8-dependent apoptotic pathway that is independent of the death effector domain of Fas-associated death domain protein. J Immunol. Jul. 15, 2001;167(2):733-40.

Borges et al., P-selectin glycoprotein ligand-1 (PSGL-1) on T helper 1 but not on T helper 2 cells binds to P-selectin and supports migration into inflamed skin. J Exp Med. Feb. 3, 1997;185(3):573-8.

Borges et al., The binding of T cell-expressed P-selectin glycoprotein ligand-1 to E- and P-selectin is differentially regulated. J Biol Chem. Nov. 7, 1997;272(45):28786-92.

Borges et al., The P-selectin glycoprotein ligand-1 is important for recruitment of neutrophils into inflamed mouse peritoneum. Blood. Sep. 1, 1997;90(5):1934-42.

Campbell, Monoclonal antibody technology. 1985. Elsevier Science Publishers. Preface and pp. 1-32.

Carpenter et al., A humanized non-FcR-binding anti-CD3 antibody, visilizumab, for treatment of steroid-refractory acute graft-versus-host disease. Blood. Apr. 15, 2002;99(8):2712-9.

Chen et al., Cross-linking of P-selectin glycoprotein ligand-1 induces death of activated T cells. Blood. Nov. 15, 2004;104(10):3233-42. Epub Jun. 15, 2004.

Diacovo et al., Interactions of human alpha/beta and gamma/delta T lymphocyte subsets in shear flow with E-selectin and P-selectin. J Exp Med. Mar. 1, 1996;183(3):1193-203.

Dimitroff et al., Glycosylation-dependent inhibition of cutaneous lymphocyte-associated antigen expression: implications in modulating lymphocyte migration to skin. Blood. Jan. 15, 2003;101(2):602-10. Epub Sep. 5, 2002.

Evangelista et al., Platelet/polymorphonuclear leukocyte interaction: P-selectin triggers protein-tyrosine phosphorylation-dependent CD11b/CD18 adhesion: role of PSGL-1 as a signaling molecule. Blood. Feb. 1, 1999;93(3):876-85.

Faraday et al., Leukocytes can enhance platelet-mediated aggregation and thromboxane release via interaction of P-selectin glycoprotein ligand 1 with P-selectin. Anesthesiology. Jan. 2001;94(1):145-51.

Frenette et al., P-Selectin glycoprotein ligand 1 (PSGL-1) is expressed on platelets and can mediate platelet-endothelial interactions in vivo. J Exp Med. Apr. 17, 2000;191(8):1413-22.

Fuhlbrigge et al., Cutaneous lymphocyte antigen is a specialized form of PSGL-1 expressed on skin-homing T cells. Nature. Oct. 30, 1997;389(6654):978-81.

Genestier et al., Fas-independent apoptosis of activated T cells induced by antibodies to the HLA class I alpha1 domain. Blood. Nov. 1, 1997;90(9):3629-39.

Herron et al., Intracellular parasitism by the human granulocytic ehrlichiosis bacterium through the P-selectin ligand, PSGL-1. Science. Jun. 2, 2000;288(5471):1653-6.

Hirata et al., P-Selectin glycoprotein ligand 1 (PSGL-1) is a physiological ligand for E-selectin in mediating T helper 1 lymphocyte migration. J Exp Med. Dec. 4, 2000;192(11):1669-75.

Hirose et al., A functional epitope on P-selectin that supports binding of P-selectin to P-selectin glycoprotein ligand-1 but not to sialyl Lewis X oligosaccharides. Int Immunol. May 1998;10(5):639-49.

Igarashi et al., Telomerase activity is induced in human peripheral B lymphocytes by the stimulation to antigen receptor. Blood. Feb. 15, 1997;89(4):1299-307.

Kaytes et al., P-selectin mediates adhesion of the human melanoma cell line NKI-4: identification of glycoprotein ligands. Biochemistry. Jul. 21, 1998;37(29):10514-21.

Kieffer et al., Neutrophils, monocytes, and dendritic cells express the same specialized form of PSGL-1 as do skin-homing memory T cells: cutaneous lymphocyte antigen. Biochem Biophys Res Commun. Jul. 20, 2001;285(3):577-87.

Laszik et al., P-selectin glycoprotein ligand-1 is broadly expressed in cells of myeloid, lymphoid, and dendritic lineage and in some nonhematopoietic cells. Blood. Oct. 15, 1996;88(8):3010-21.

Lévesque et al., PSGL-1-mediated adhesion of human hematopoietic progenitors to P-selectin results in suppression of hematopoiesis. Immunity. Sep. 1999;11(3):369-78.

Li et al., Visualization of P-selectin glycoprotein ligand-1 as a highly extended molecule and mapping of protein epitopes for monoclonal antibodies. J Biol Chem. Mar. 15, 1996;271(11):6342-8.

Moore et al., P-selectin glycoprotein ligand-1 mediates rolling of human neutrophils on P-selectin. J Cell Biol. Feb. 1995;128(4):661-71.

Sako et al., Expression cloning of a functional glycoprotein ligand for P-selectin. Cell. Dec. 17, 1993;75(6):1179-86.

Shan et al., Apoptosis of malignant human B cells by ligation of CD20 with monoclonal antibodies. Blood. Mar. 1, 1998;91(5):1644-52.

Snapp et al., A novel P-selectin glycoprotein ligand-1 monoclonal antibody recognizes an epitope within the tyrosine sulfate motif of human PSGL-1 and blocks recognition of both P- and L-selectin. Blood. Jan. 1, 1998;91(1):154-64.

Stockmeyer et al., Polymorphonuclear granulocytes induce antibody-dependent apoptosis in human breast cancer cells. J Immunol. Nov. 15, 2003;171(10):5124-9.

Trembleau et al., Pancreas-infiltrating Th1 cells and diabetes develop in IL-12-deficient nonobese diabetic mice. J Immunol. Sep. 1, 1999;163(5):2960-8.

Vachino et al., P-selectin glycoprotein ligand-1 is the major counter-receptor for P-selectin on stimulated T cells and is widely distributed in non-functional form on many lymphocytic cells. J Biol Chem. Sep. 15, 1995;270(37):21966-74.

Veldman et al., Genomic organization and chromosomal localization of the gene encoding human P-selectin glycoprotein ligand. J Biol Chem. Jul. 7, 1995;270(27):16470-5.

(56) References Cited

OTHER PUBLICATIONS

Wing et al., Mechanism of first-dose cytokine-release syndrome by CAMPATH 1-H: involvement of CD16 (FcgammaRIII) and CD11a/CD18 (LFA-1) on NK cells. J Clin Invest. Dec. 15, 1996;98(12):2819-26.

Woltmann et al., Interleukin-13 induces PSGL-1/P-selectin-dependent adhesion of eosinophils, but not neutrophils, to human umbilical vein endothelial cells under flow. Blood. May 15, 2000;95(10):3146-52.

Wu et al., Role of P-selectin and anti-P-selectin monoclonal antibody in apoptosis during hepatic/renal ischemia reperfusion injury. World J Gastroenterol. Apr. 2000;6(2):244-247.

Yago et al., IL-12 promotes the adhesion of NK cells to endothelial selectins under flow conditions. J Immunol. Aug. 1, 1998;161(3):1140-5.

Yang et al., Targeted gene disruption demonstrates that P-selectin glycoprotein ligand 1 (PSGL-1) is required for P-selectin-mediated but not E-selectin-mediated neutrophil rolling and migration. J. Exp Med. Dec. 20, 1999;190(12):1769-82.

Genbank Submission; NIH/NCBI, Accession No. AAQ51275.1; McFadden et al.; Sequence 3 from U.S. Pat. No. 6,589,933; Aug. 17, 2003.

Yolcu et al., Cell membrane modification for rapid display of proteins as a novel means of immunomodulation: FasL-decorated cells prevent islet graft rejection. Immunity. Dec. 2002;17(6):795-808.

Truman et al., The larval eclosion hormone neurons in Manduca sexta: identification of the brain-proctodeal neurosecretory system. J Exp Biol. 1989;147:457-70.

Kataoka et al., Isolation and primary structure of the eclosion hormone of the tobacco hornworm, Manduca sexta. Biochem Biophys Res Commun. 1987;146(2). Abstract only retrieved from http://www.ncbi.nlm.nih.gov/pubmed/3304284 on Jan. 16, 2014, 1 page.

Koeller et al., Chemoenzymatic synthesis of a PSGL-1 N-Terminal glycopeptide containing tyrosine sulfate and alpha-O-linked sialyl lewis X. J Am Chem Soc. 2000;122(17):4241-2. Epub Apr. 15, 2000.

\* cited by examiner

```
                        SEQUENCE LISTING

<160> NUMBER OF SEQ ID NOS: 26

<210> SEQ ID NO 1
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Tyr, Trp, His, or Met
<220> FEATURE:
<221> NAME/KEY: VARIANT
<222> LOCATION: 2
<223> OTHER INFORMATION: Xaa = Asp
<220> FEATURE:
<221> NAME/KEY: VARIANT
<222> LOCATION: 3
<223> OTHER INFORMATION: Xaa = Ser, Phe, Pro, Glu, or His
<220> FEATURE:
<221> NAME/KEY: VARIANT
<222> LOCATION: 4
<223> OTHER INFORMATION: Xaa = any amino acid that naturally occurring
      in animals
<220> FEATURE:
<221> NAME/KEY: VARIANT
<222> LOCATION: 5
<223> OTHER INFORMATION: Xaa = Pro, Tyr, His, or Trp

<400> SEQUENCE: 1

Xaa Xaa Xaa Xaa Xaa
 1               5

<210> SEQ ID NO 2
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Asp
<220> FEATURE:
<221> NAME/KEY: VARIANT
<222> LOCATION: 2
<223> OTHER INFORMATION: Xaa = Tyr, Met, Asn, Trp, or Phe
<220> FEATURE:
<221> NAME/KEY: VARIANT
<222> LOCATION: 3
<223> OTHER INFORMATION: Xaa = Phe or Leu
<220> FEATURE:
<221> NAME/KEY: VARIANT
<222> LOCATION: 4
<223> OTHER INFORMATION: Xaa = Pro
<220> FEATURE:
<221> NAME/KEY: VARIANT
<222> LOCATION: 5
```

```
<223> OTHER INFORMATION: Xaa = Glu

<400> SEQUENCE: 2

Xaa Xaa Xaa Xaa Xaa
 1               5

<210> SEQ ID NO 3
<211> LENGTH: 4
<212> TYPE: PRT
<213> ORGANISM: Artificial sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Pro or Ala
<220> FEATURE:
<221> NAME/KEY: VARIANT
<222> LOCATION: 2
<223> OTHER INFORMATION: Xaa = Met
<220> FEATURE:
<221> NAME/KEY: VARIANT
<222> LOCATION: 3
<223> OTHER INFORMATION: Xaa = Glu or Ser
<220> FEATURE:
<221> NAME/KEY: VARIANT
<222> LOCATION: 4
<223> OTHER INFORMATION: Xaa = Ile

<400> SEQUENCE: 3

Xaa Xaa Xaa Xaa
 1

<210> SEQ ID NO 4
<211> LENGTH: 13
<212> TYPE: PRT
<213> ORGANISM: Artificial sequence
<220> FEATURE:
<223> OTHER INFORMATION: Synthetically generated peptide

<400> SEQUENCE: 4

Trp Pro Glu Asp Ser Ser Tyr Asp Ser Trp Pro Arg Gly
 1               5                  10

<210> SEQ ID NO 5
<211> LENGTH: 11
<212> TYPE: PRT
<213> ORGANISM: Artificial sequence
<220> FEATURE:
<223> OTHER INFORMATION: Synthetically generated peptide

<400> SEQUENCE: 5

Leu Asp Tyr Asp Phe Leu Pro Glu Thr Glu Pro
 1               5                  10

<210> SEQ ID NO 6
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 6

Thr Ala Thr Trp Asp Pro Asp Tyr Phe Ser Asp Ser
 1               5                  10

<210> SEQ ID NO 7
<211> LENGTH: 13
<212> TYPE: PRT
```

```
<213> ORGANISM: Artificial sequence
<220> FEATURE:
<223> OTHER INFORMATION: Synthetically generated peptide

<400> SEQUENCE: 7

Ala Glu Thr Asp Tyr Asp Pro Asp His Phe Thr Pro Gly
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetically generated peptide

<400> SEQUENCE: 8

Asp Ala Arg Tyr Ser His Asp Pro Ala Trp Pro Tyr Gly
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetically generated peptide

<400> SEQUENCE: 9

Ala Gly Gln Lys Trp Asp Pro Glu Trp Pro His Ser Gly
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetically generated peptide

<400> SEQUENCE: 10

Glu Pro Asn Met Asp Pro Asn Trp Asp Ser Gly
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetically generated peptide

<400> SEQUENCE: 11

Lys Ser His Tyr Asp Glu Ser Trp Trp Tyr Asn Gly Gly
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 12

Tyr Asp His His Trp Thr Asn Pro Pro Thr Gln Lys
1               5                   10

<210> SEQ ID NO 13
<211> LENGTH: 12
<212> TYPE: PRT
<213> ORGANISM: Artificial sequence
```

```
<220> FEATURE:
<223> OTHER INFORMATION: Synthetically generated peptide

<400> SEQUENCE: 13

Tyr Asp His His Trp Pro Arg Asp Asp Ile Ala Pro
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 14

Gln Asp Thr Trp Tyr Pro Asp Tyr Phe Pro Glu Ser
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 15

Ser His Thr Leu Leu Asn Asp Met Phe Pro Glu Ser
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 16

Ser Pro Leu Arg Asp Asn Phe Pro Glu Thr Leu Trp
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetically generated peptide

<400> SEQUENCE: 17

Asp Tyr Met Asp Asn Phe Pro Glu Glu Asn
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 18

Gln Leu Val Gln Asp Trp Leu Pro Glu Glu Ser His
1               5                   10

<210> SEQ ID NO 19
<211> LENGTH: 13
<212> TYPE: PRT
<213> ORGANISM: Artificial sequence
<220> FEATURE:
```

<223> OTHER INFORMATION: Synthetically generated peptide

<400> SEQUENCE: 19

Tyr Leu Asp Tyr Asp Phe Leu Pro Glu Thr Glu Pro Pro
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 20

Tyr Thr Pro Met Pro Met Glu Ile Ser His Ser Ala
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 21

Met Asn Asp Lys Tyr Ile Pro Met Ser Ile Ser Ala
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 22

Lys Ile Pro His Lys Thr Leu Val Pro Met Glu Ile
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 23

Thr Asp Ser Ala Ala Met Glu Ile Gln Thr Thr Gln
1               5                   10

<210> SEQ ID NO 24
<211> LENGTH: 4
<212> TYPE: PRT
<213> ORGANISM: Artificial sequence
<220> FEATURE:
<223> OTHER INFORMATION: Synthetically generated peptide

<400> SEQUENCE: 24

Pro Met Glu Ile
1

<210> SEQ ID NO 25
<211> LENGTH: 4
<212> TYPE: PRT
<213> ORGANISM: Artificial sequence
<220> FEATURE:
<223> OTHER INFORMATION: Synthetically generated peptide

```
<400> SEQUENCE: 25

Ala Met Glu Ile
 1

<210> SEQ ID NO 26
<211> LENGTH: 4
<212> TYPE: PRT
<213> ORGANISM: Artificial sequence
<220> FEATURE:
<223> OTHER INFORMATION: Synthetically generated peptide

<400> SEQUENCE: 26

Ala Met Ser Ile
 1
```

T-CELL DEATH-INDUCING EPITOPES

RELATED APPLICATION

This application is a continuation of patent application Ser. No. 11/127,804 filed May 11, 2005, now abandoned, which claims the benefit under 35 U.S.C. §119(e) of U.S. provisional Patent Application No. 60/570,161, filed May 11, 2004, the disclosures of both of which are incorporated herein by reference.

BACKGROUND

Control of unwanted immune responses is critical in treating autoimmune diseases, transplant rejection, allergic diseases, and T-cell-derived cancers. The activity of overly aggressive T-cells can be contained by immunosuppression or by induction of immunological tolerance. Apoptosis is believed to be involved in maintaining proper functions of the immune system and removing unwanted cells, such as overly aggressive T-cells (Kabelitz et al. (1993) Immunol Today 14, 338-340; and Raff (1992) Nature 356, 397-399).

SUMMARY

This invention relates to T-cell death-inducing epitopes. The epitopes can be used for, among others, selecting compounds that bind to the epitopes. Such compounds are useful in treating diseases involving overly aggressive T-cells. Examples of such diseases include autoimmune diseases, transplant rejection, allergic diseases, and T-cell-derived cancers.

In one aspect, the invention features a three-dimensional conformation of an isolated epitope. Binding of a ligand to the epitope on activated T-cells induces death of the cells. Such an epitope is represented by:

(1)  $X_1$-$X_2$-$X_3$-$X_4$-$X_5$,  (SEQ ID NO: 1)

where
 $X_1$ is Tyr, Trp, His, or Met;
 $X_2$ is Asp;
 $X_3$ is Ser, Phe, Pro, Glu, or His;
 $X_4$ is any amino acid that naturally occurring in animals; and
 $X_5$ is Pro, Tyr, His, or Trp;

(2)  $X_6$-$X_7$-$X_8$-$X_9$-$X_{10}$,  (SEQ ID NO: 2)

where
 $X_6$ is Asp;
 $X_7$ is Tyr, Met, Asn, Trp, or Phe;
 $X_8$ is Phe or Leu;
 $X_9$ is Pro; and
 $X_{10}$ is Glu; or (3)  $X_{11}$-$X_{12}$-$X_{13}$-$X_{14}$,  (SEQ ID NO: 3)

where
 $X_{11}$ is Pro;
 $X_{12}$ is Met;
 $X_{13}$ is Glu or Ser; and
 $X_{14}$ is Ile.

Any of those epitopes described above can be, e.g., a polypeptide, an interacting region of two polypeptides, a carbohydrate moiety, a glycoprotein, or any conformational, functional equivalent thereof.

In another aspect, the invention features an isolated polypeptide containing $X_1$-$X_2$-$X_3$-$X_4$-$X_5$, $X_6$-$X_7$-$X_8$-$X_9$-$X_{10}$, or $X_{11}$-$X_{12}$-$X_{13}$-$X_{14}$. Binding of a ligand to the polypeptide on activated T-cells induces death of the cells. In one embodiment, the polypeptide contains 4 to 400 amino acids (e.g., any integer between 4 and 400, inclusive). For example, the polypeptide can be $X_1$-$X_2$-$X_3$-$X_4$-$X_5$ (SEQ ID NO:1), $X_6$-$X_7$-$X_8$-$X_9$-$X_{10}$ (SEQ ID NO:2), $X_{11}$-$X_{12}$-$X_{13}$-$X_{14}$ (SEQ ID NO:3), or any of SEQ ID NOs:4, 6-18, and 20-22.

An "isolated epitope" or "isolated polypeptide" refers to an epitope or polypeptide substantially free from naturally associated molecules, i.e., it is at least 75% (e.g., any number between 75% and 100%, inclusive) pure by dry weight. Purity can be measured by any appropriate standard method, for example, by column chromatography, polyacrylamide gel electrophoresis, or HPLC analysis. An isolated epitope or polypeptide of the invention can be purified from a natural source, produced by recombinant DNA techniques, or by chemical methods.

In still another aspect, the invention features a novel compound that binds to one of the above-described epitopes. The compound can be any kind of molecule, including antibodies such as monoclonal antibodies. A compound of the invention can be used for detecting an epitope of the invention and for inducing death of activated T-cells.

Also within the scope of the invention is a method of producing antibodies. The method involves administering to a subject an effective amount of one of the above-described epitopes (e.g., polypeptides). The antibodies can be used for detecting an epitope of the invention or for inducing death of activated T-cells.

The invention also features a method of identifying a candidate compound (e.g., a monoclonal antibody) for inducing death of activated T-cells. The method involves contacting a test compound with an epitope of the invention and determining whether the test compound binds to the epitope. If the test compound binds to the epitope, it is a candidate for inducing death of activated T-cells.

The invention further features a method of inducing death of activated T-cells by contacting activated T-cells with a compound of the invention.

In yet another aspect, the invention features a pharmaceutical composition containing a pharmaceutically acceptable carrier and (1) an epitope of the invention such as a polypeptide, or (2) a compound that binds to the epitope.

The invention provides compositions and methods for treating diseases involving overly aggressive T-cells such as autoimmune diseases, transplant rejection, allergic diseases, and T-cell-derived cancers. The details of one or more embodiments of the invention are set forth in the accompanying description below. Other features, objects, and advantages of the invention will be apparent from the detailed description.

DETAILED DESCRIPTION

This invention is based on the unexpected discovery that activated T-cells can be induced to undergo apoptosis and be depleted by engagement of new T-cell death-inducing epitopes. Depletion of activated T-cells are particularly useful for treating conditions associated with an excessive or unwanted T-cell-mediated immune response or T-cell proliferation. For example, depletion of activated T-cells can result in reduction or elimination of undesirable T-cell activity or proliferation related to autoimmune diseases, transplant rejection, allergic diseases, or T-cell-derived cancers.

Accordingly, the invention features a three-dimensional conformation of an isolated epitope. Binding of a ligand to the epitope on activated T-cells induces death of the cells. The epitope is represented by $X_1$-$X_2$-$X_3$-$X_4$-$X_5$, $X_6$-$X_7$-$X_8$-$X_9$-$X_{10}$, or $X_{11}$-$X_{12}$-$X_{13}$-$X_{14}$. The three-dimensional conformation of $X_1$-$X_2$-$X_3$-$X_4$-$X_5$, $X_6$-$X_7$-$X_8$-$X_9$-$X_{10}$, or $X_{11}$-$X_{12}$-$X_{13}$-$X_{14}$ can be determined, e.g., using computer modeling programs as described in Duggan et al., (1995) J Med Chem. 38:3332-41 and Toogood (2002) J Med Chem. 45: 1543-57. Epitopes of conformational, functional equivalence can be designed in accordance with the three-dimensional conformation of $X_1$-$X_2$-$X_3$-$X_4$-$X_5$, $X_6$-$X_7$-$X_8$-$X_9$-$X_{10}$, or $X_{11}$-$X_{12}$-$X_{13}$-$X_{14}$, prepared using methods known in the art, and tested for their abilities to be involved in induction of death of activated T-cells by methods such as that described in the example below. See, e.g., Barbas et al. (2001) Phage display. A laboratory manual. CSHL Press; Parmley et al. (1998) Gene 73, 305-318; Scott et al. (1990) Science 249, 386-390; U.S. Patent Application No. 20030049252 A1; WO 03/013603 A1; Osborne (1996) Curr Opin Immunol 8:245-248; Lin et al. (1997) J. Imrnunol. 158, 598-603; Zhang et al. (1995) Nature 377, 348-350; Lai et al. (1995) Eur J Immunol 25, 3243-3248; Mollereau et al. (1996) J Immunol 156, 3184-3190; and Gribben et al. (1995) Proc Natl Acad Sci USA 92, 811-815.

As used herein, an "activated T-cell" is a T-cell having a higher frequency, rate, or extent of proliferation than that of a non-activated T-cell. "Death" of a cell includes programmed cell death, i.e., apoptosis. "Induction of cell death" by an agent occurs when a population of cells treated with the agent exhibits a higher death rate compared to an untreated cell population. For example, the percentage of in vitro activated T-cells undergoing apoptosis is about doubled when treated with monoclonal antibodies m128-9F9, m152-15A7, or m166-43B6 compared to that of untreated cells, as determined by armexin V staining and FACS analysis (see the example below).

The invention also features an isolated polypeptide containing $X_1$-$X_2$-$X_3$-$X_4$-$X_5$, $X_6$-$X_7$-$X_8$-$X_9$-$X_{10}$, or $X_{11}$-$X_{12}$-$X_{13}$-$X_{14}$. The polypeptide can be used for identifying compounds that induce death of activated T-cells. Binding of such a compound to the polypeptide expressed on the surface of activated T-cells induces cell death. Further, free polypeptides (i.e., those not expressed on the cell surface) can inhibit unwanted cell death by competing for endogenous death-inducing ligands with the cell-surface polypeptides. The length or sequence of the polypeptide may vary for these uses. A polypeptide of the invention can be obtained, e.g., as an isolated T-cell surface protein, a synthetic polypeptide, or a recombinant polypeptide. To prepare a recombinant polypeptide, a nucleic acid encoding it can be linked to another nucleic acid encoding a fusion partner, e.g., Glutathione-S-Transferase (GST), 6×-His epitope tag, or M13 Gene 3 protein. The resultant fusion nucleic acid expresses in suitable host cells a fusion protein that can be isolated by standard methods. The isolated fusion protein can be further treated, e.g., by enzymatic digestion, to remove the fusion partner and obtain the recombinant polypeptide of this invention.

An epitope of the invention or a polypeptide of the invention can be used to generate antibodies in animals (for production of antibodies) or humans (for treatment of diseases). Methods of making monoclonal and polyclonal antibodies and fragments thereof in animals are known in the art. See, for example, Harlow and Lane, (1988) Antibodies: A Laboratory Manual, Cold Spring Harbor Laboratory, New York. The term "antibody" includes intact molecules as well as fragments thereof, such as Fab, $F(ab')_2$, Fv, scFv (single chain antibody), and dAb (domain antibody; Ward, et. al. (1989) Nature, 341, 544). These antibodies can be used for detecting the epitope, e.g., in identifying a compound that binds to the epitope (see below). The antibodies that are capable of inducing death of activated T-cells are also useful for treating diseases such as autoimmune diseases, transplant rejection, allergic diseases, or T-cell-derived cancers. In general, an epitope of the invention, e.g., a polypeptide, can be coupled to a carrier protein, such as KLH, mixed with an adjuvant, and injected into a host animal. Antibodies produced in that animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and Corynebacterium parvum.

Polyclonal antibodies, heterogeneous populations of antibody molecules, are present in the sera of the immunized subjects. Monoclonal antibodies, homogeneous populations of antibodies to a particular antigen, can be prepared using standard hybridoma technology (see, for example, Kohler et al. (1975) Nature 256, 495; Kohler et al. (1976) Eur J Immunol 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc Natl Acad Sci USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) Proc Natl Acad Sci USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

The invention further features a novel compound that binds to an epitope of the invention and induces death of activated T-cells. Such a compound can be designed, e.g., using computer modeling programs, according to the three-dimensional conformation of the epitope, and synthesized using methods known in the art. It can also be identified by library screening as described below.

The test compounds can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, the "one-bead one-compound" libraries, and antibody libraries. See, e.g., Zuckermann et al. (1994) J Med Chem 37, 2678-85; Lam (1997) Anticancer Drug Des 12, 145; Lam et al. (1991) Nature 354, 82; Houghten et al. (1991) Nature 354, 84; and Songyang et al. (1993) Cell 72, 767.

Examples of methods for the synthesis of molecular libraries can be found in the art, for example, in: DeWitt et al. (1993) PNAS USA 90, 6909; Erb et al. (1994) PNAS USA 91, 11422; Zuckermann et al. (1994) J Med Chem 37, 2678; Cho et al. (1993) Science 261, 1303; Carrell et al. (1994) Angew Chem Int Ed Engl 33, 2059; Carell et al. (1994) Angew Chem Int Ed Engl 33, 2061; and Gallop et al. (1994) J Med Chem 37, 1233.

Libraries of compounds may be presented in solution (e.g., Houghten (1992) Biotechniques 13, 412-421), or on beads (Lam (1991) Nature 354, 82-84), chips (Fodor (1993) Nature 364, 555-556), bacteria (U.S. Pat. No. 5,223,409), spores (U.S. Pat. No. 5,223,409), plasmids (Cull et al. (1992) PNAS USA 89, 1865-1869), or phages (Scott and Smith (1990) Science 249, 386-390; Devlin (1990) Science 249, 404-406; Cwirla et al. (1990) PNAS USA 87, 6378-6382; Felici (1991) J Mol Biol 222, 301-310; and U.S. Pat. No. 5,223,409).

To identify a candidate compound for inducing death of activated T-cells, an epitope of the invention is contacted with a test compound, and the binding of the compound to the epitope is evaluated. If the compound binds to the epitope, it is a candidate for inducing death of activated T-cells.

The screening assay can be conducted in a variety of ways. For example, one method involves anchoring the epitope (or an epitope-containing molecule, e.g., a polypeptide or a fusion protein) or the test compound onto a solid phase and detecting an epitope-test compound complex formed on the solid phase at the end of the reaction. In practice, microtiter plates may conveniently be utilized as the solid phase. The anchor component may be immobilized by non-covalent or covalent attachments. Non-covalent attachment may be accomplished by simply coating the solid surface with a solution of the anchor component and drying the plates. Alternatively, an immobilized antibody (e.g., a monoclonal antibody) specific for the anchor component may be used to immobilize the anchor component to the solid surface. The non-anchor component is added to the solid surface coated with the anchor component. After the reaction is complete, unbound fraction of the non-anchor components is removed (e.g., by washing) under conditions such that any complexes formed remain immobilized on the solid surface. Detection of these complexes can be accomplished in a number of ways. Where the non-anchor component is pre-labeled, detection of the label immobilized on the solid surface indicates that complexes were formed. Where the non-anchor component is not pre-labeled, an indirect label can be used to detect complexes formed on the surface, e.g., using an antibody specific for the non-anchor component (the antibody, in turn, may be directly labeled or indirectly labeled with a labeled anti-Ig antibody).

Alternatively, the reaction can be conducted in a liquid phase. The complexes are separated from unbound components, e.g., using an immobilized antibody specific for the epitope (or the epitope-containing molecule) or the test compound. The complexes are then detected, e.g., using a labeled antibody specific for the other component.

The candidate compound can be validated by ascertaining its ability to induce death of activated T-cells, using the method described in the example below, or any other method know in the art. The validated compound can be used for inducing death of activated T-cells and for treating diseases such as autoimmune diseases, transplant rejection, allergic diseases, or T-cell-derived cancers.

The invention provides a method of inducing death of activated T-cells, e.g., by contacting activated T-cells with a compound of the invention in vitro, or by administering to a subject in need thereof an effective amount of a compound of the invention. Subjects to be treated can be identified as having or being at risk for acquiring a condition characterized by an excessive or unwanted T-cell-mediated immune response, e.g., patients suffering from autoimmune diseases, transplant rejection, allergic diseases, or T-cell-derived cancers. This method can be performed alone or in conjunction with other drugs or therapy.

The term "treating" is defined as administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result, e.g., as described above, in a treated subject.

Exemplary diseases to be treated include, but are not limited to, diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, AIDS, and T-cell neoplasms such as leukemias or lymphomas.

In one in vivo approach, a therapeutic composition (e.g., a composition containing an epitope of the invention, a polypeptide of the invention, or a compound of the invention) is administered to the subject. Generally, the epitope, the polypeptide, or the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Also within the scope of this invention is a pharmaceutical composition that contains a pharmaceutically acceptable carrier and an effective amount of a compound of the invention. The pharmaceutical composition can be used to treat diseases described above. The pharmaceutically acceptable carrier includes a solvent, a dispersion medium, a coating, an antibacterial and antifungal agent, and an isotonic and absorption delaying agent.

The pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. See, e.g., the examples below. Briefly, the composition can be tested for its ability to induce death of activated T-cells in vitro. For in vivo studies, the composition can be injected into an animal (e.g., a mouse model) and its therapeutic effects are then accessed. Based on the results, an appropriate dosage range and administration route can be determined.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Preparation of a Mouse Spleen Cell Suspension

Mouse spleen was immersed in 8 ml of Hank's balanced salt solution (HBSS), gently minced with a sterile cover slip, transferred to a 15 ml centrifuge tube (Costar), and spun at 200×g for 5 minutes. The supernatant was discarded, and the cell pellet was resuspended in the residual buffer by gently tapping the wall. The contaminating red blood cells (RBC) were lysed by addition of 1 ml of RBC lysis buffer (0.6 M $NH_4Cl$, 0.17 M Tris-base, pH 7.65), followed by a 2 min incubation at room temperature and rapid quenching with 9 ml of HBSS. The cells were pelleted at 200×g for 5 minutes, washed twice, and resuspended in RPMI medium. The concentration and viability of the cells in the mixture were determined with a hemocytometer (Cambridge Scientific Inc.) and Trypan blue exclusion.

Preparation of Anti-T-Cell, Apoptosis-Inducing Monoclonal Antibodies

T-cell apoptosis-inducing monoclonal antibodies were generated by immunizing a mouse with Concanovalin A-activated human T-cells and screened for their abilities to bind to activated human T-cells and subsequently to induce T-cell apoptosis. The monoclonal antibodies were prepared according to the well-known cell fusion methods of Kohler and Milstein ((1976) Euro J Immunol 6, 511-519) to produce a hybridoma secreting desired antibodies. Three hybridomas generated according to these methods secreted monoclonal antibodies, designated m128-9F9, m152-15A7, and m166-43B6, respectively, that were able to induce T-cell apoptosis in vitro.

Concentrated culture supernatant of each hybridoma was spun at 20000×g for 10 minutes, and the supernatant was diluted at a 1:1 ratio with the binding buffer (0.1 M sodium acetate, pH 5.0). A protein G column (approximately 1 ml bed volume) was washed three times with 3-5 ml of the binding buffer. The cleared culture supernatant was loaded onto the protein G column, and the flow-through was collected and reloaded to the column. The column was then washed with 6-10 ml of the binding buffer, and the bound antibody was eluted from the column with 5 ml of the elution buffer (0.1 M glycine-HCl, pH 2.8). Each fraction contained 1 ml of the eluted antibody, and the eluted fraction was adjusted to the neutral pH by mixing each 1 ml fraction with 50 microliters of 1 M Tris-HCl, pH 7.5. Fractions containing the antibody were pooled and dialyzed against 2 liters of PBS, pH 7.4 three times for three hours per dialysis. Protein concentrations in the antibody samples were determined following the procedure described by Bradford using the Bio-Rad Protein Assay (BIO-RAD, Hercules, Calif.).

Induction of Death of Activated Human T-Cells by Monoclonal Antibodies

Activated T cells (see above) were resuspended to a final concentration of $5 \times 10^5$ cells/ml in RPMI medium containing 5 ng/ml of IL-2, and treated with control Ig, m128-9F9, m152-15A7, or m166-43B6.

It is well known that T-cell death-inducing antibodies can be used as therapeutic agents to treat T-cell-related diseases such as transplantation rejections, autoimmune diseases, and allergy. Three monoclonal antibodies against human T-cells were generated, and the capabilities of these monoclonal antibodies to induce apoptosis of activated human T-cells were examined. Culture supernatants containing monoclonal antibodies secreted by hybridoma cell line m128-9F9, m152-15A7, or m166-43B6 were incubated with either non-activated human T-cells (Day 0) or in vitro activated human T-cells (Day7) for 6 hours. Cells were stained with annexin V after incubation, and subjected to FACS analysis. CD3-positive cells were gated to ensure counting of either in vitro activated human T-cells or resting human T-cells. The apoptotic cells were annexin V staining-positive. Table 1 summarizes the percentage of apoptotic T-cells among all of the T-cells scanned. Unexpectedly, monoclonal antibodies secreted by hybridoma cell lines m128-9F9, m152-15A7, and m166-43B6 induced death of in vitro activated human T-cells but did not affect non-activated human T-cells. This capability of inducing apoptosis of activated T-cells yet sparing the resting T-cells is a unique feature of the apoptotic pathway and is a dominating feature of therapeutic reagents targeting T-cell-mediated diseases.

TABLE 1

Percentage of apoptotic T-cells

|  | Untreated | Anti-myc | m128-9F9 | Untreated | Anti-myc | m152-15A7 | m166-43B6 |
| --- | --- | --- | --- | --- | --- | --- | --- |
| Day 0 | 4.17 | 6.67 | 5.82 | 18.18 | 15.52 | 5.23 | 6.57 |
| Day 7 | 12.63 | 13.36 | 28.71 | 24.18 | 23.08 | 51.66 | 49.44 |

Identification of T-Cell Death-Inducing Epitopes

In order to identify death-inducing epitopes recognized by monoclonal antibodies m128-9F9, m152-15A7, and m166-43B6, these monoclonal antibodies were used to screen for consensus binding sequences in a polypeptide library (Ph. D.-12™ Phage Display Peptide Library Kit, New England Biolabs, Inc.). The library contained various 12-mer peptides linked to the 406-aa M13 Gene 3 protein. 96-well microtiter plates were coated with 50 μl/well antibodies at the concentration of 10 μg/ml in 0.1 M NaHCO$_3$ (pH 8.6) coating buffer overnight at 4° C. After the wash, the plates were blocked by incubation with the blocking buffer containing 0.1 M NaHCO$_3$ (pH 8.6), 5 mg/ml BSA, 0.02% NaN$_3$ (150 μl/well) for at least one hour at 4° C. Plates were then incubated with fusion proteins from the polypeptide library described above at various concentrations for one hour at room temperature. After the wash with 0.5% Tween containing TBS, the bound fusion proteins were eluted with 1 mg/ml BSA containing 0.2 M Glycine-HCl (pH 2.2) buffer and neutralized with 1 M Tris-HCl (pH 9.1). The amino acid sequences of eluted fusion proteins were then determined.

The polypeptide sequences bound by monoclonal antibody m128-9F9 are shown below:

| WPEDSSYDSWPRG | SEQ ID NO: 4 |
| LDYDFLPETEP | SEQ ID NO: 5 |
| TATWDPDYFSDS | SEQ ID NO: 6 |
| AETDYDPDHFTPG | SEQ ID NO: 7 |
| DARYSHDPAWPYG | SEQ ID NO: 8 |
| AGQKWDPEWPHSG | SEQ ID NO: 9 |
| EPNMDPNWASPSG | SEQ ID NO: 10 |
| KSHYDESWWYNGG | SEQ ID NO: 11 |
| YDHHWTNPPTQK | SEQ ID NO: 12 |
| YDHHWPRDDIAP | SEQ ID NO: 13 |

A consensus polypeptide sequence of $X_1$-$X_2$-$X_3$-$X_4$-$X_5$ was obtained, where $X_1$=Y/W/H/M, $X_2$=D, $X_3$=S/F/P/E/H, $X_4$=any amino acid, and $X_5$=P/Y/H/W.

The polypeptide sequences bound by monoclonal antibody m166-43B6 are shown below:

| QDTWYPDYFPES | SEQ ID NO: 14 |
| SHTLLNDMFPES | SEQ ID NO: 15 |
| SPLRDNFPETLW | SEQ ID NO: 16 |
| ASPYMDNFPEEN | SEQ ID NO: 17 |
| QLVQDWLPEESH | SEQ ID NO: 18 |
| YLDYDFLPETEPP | SEQ ID NO: 19 |

A consensus polypeptide sequence of $X_6$-$X_7$-$X_8$-$X_9$-$X_{10}$ was obtained, where $X_6$=D, $X_7$=Y/M/N/W/F, $X_8$=F or L, $X_9$=P, and $X_{10}$=E.

The polypeptide sequences bound by monoclonal antibody m152-15A7 are shown below:

| YTPMPMEISHSA | SEQ ID NO: 20 |
| MNDKYIPMSISA | SEQ ID NO: 21 |
| KIPHKTLVPMEI | SEQ ID NO: 22 |
| TDSAAMEIQTTQ | SEQ ID NO: 23 |

A consensus polypeptide sequence of $X_{11}$-$X_{12}$-$X_{13}$-$X_{14}$ was obtained, where $X_{11}$=P/A, $X_{12}$=M, $X_{13}$=E/S, and $X_{14}$=I.

ELISA Assay of T-Cell Death-Inducing Epitopes Recognized by Monoclonal Antibodies In order to identify the specificities of the death-inducing epitopes recognized by the monoclonal antibodies described above, the sandwich ELISA was conducted. Serial dilutions (from 0.0017 fmol to 17 fmol) of the epitope-containing polypeptides were incubated with monoclonal antibodies m128-9F9, m152-15A7, or m166-43B6 pre-coated on the ELISA plates to determine their binding affinities.

96-well microtiter plates were coated with 50 μl/well antibodies at the concentration of 1 μg/ml overnight at 4° C. Plates were blocked by incubation with 0.25% of BSA in PBS (150 μl/well) for 1 hour at 37° C. Plates were then incubated with fusion proteins containing various polypeptides for 2 hours at room temperature. After being washed 4 times with PBS containing 0.05% of Tween 20 (PBST), plates were then incubated with antibodies specific for the fusion partner at 2 μg/ml for 1.5 hours at room temperature. After incubation, plates were washed 4 times with PBST. 50

µl of 1 to 3000 times diluted specific goat anti-fusion partner antibodies conjugated with alkaline phosphotase (AP) was then added to each well, and the plates were incubated for 1 hour at 37° C. Enzyme reaction was carried out by adding 50 ul of AP substrate solution (1 AP substrate tablet dissolved in 5 ml of substrate buffer). The results confirmed that all of the selected polypeptides bind specifically to their corresponding antibodies used for selection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the invention.

What is claimed is:

1. An isolated polypeptide comprising SEQ ID NO: 20 or SEQ ID NO: 22, wherein binding of a ligand to the polypeptide on activated T-cells induces death of the cells.

2. An isolated polypeptide comprising SEQ ID NO: 21, wherein binding of a ligand to the polypeptide on activated T-cells induces death of the cells.

3. The polypeptide of claim 2, wherein the polypeptide is 12 to 1500 amino acids in length.

4. The polypeptide of claim 3, wherein the polypeptide is 12 to 150 amino acids in length.

5. The polypeptide of claim 4, wherein the polypeptide is 12 to 15 amino acids in length.

6. The polypeptide claim 2, wherein the polypeptide is SEQ ID NO: 21.

7. A pharmaceutical composition comprising the polypeptide of claim 2.

8. A pharmaceutical composition comprising the polypeptide of claim 1.

* * * * *